United States Patent [19]
Griffiths et al.

[11] Patent Number: 5,442,075
[45] Date of Patent: Aug. 15, 1995

[54] PROCESS FOR THE PRODUCTION OF 2-SUBSTITUTED 5-CHLORIMIDAZOLE-4-CARBALDEHYDES

[75] Inventors: Gareth Griffiths, Visp; Renë Imwinkelried, Brig-Glis; Jacques Gosteli, Basel, all of Switzerland

[73] Assignee: Lonza Ltd., Gampel/Valais, Switzerland

[21] Appl. No.: 208,955

[22] Filed: Mar. 11, 1994

Related U.S. Application Data

[63] Continuation-in-part of Ser. No. 203,583, Mar. 1, 1994, abandoned.

[30] Foreign Application Priority Data

Mar. 12, 1993 [CH] Switzerland .............. 749/93

[51] Int. Cl.$^6$ .................. C07D 233/68; C07D 233/96
[52] U.S. Cl. ................. 548/316.4; 548/333.5
[58] Field of Search ................... 548/316.4, 333.5

[56] References Cited

U.S. PATENT DOCUMENTS 4,355,040 10/1982 Furukawa et al. .......... 548/336 X

FOREIGN PATENT DOCUMENTS

| | | |
|---|---|---|
| 0028834 | 5/1981 | European Pat. Off. . |
| 0430709 | 6/1991 | European Pat. Off. . |
| 0450566 | 10/1991 | European Pat. Off. . |
| 2804435 | 8/1978 | Germany . |
| 525676 | 8/1976 | U.S.S.R. .......... 548/333.5 |

OTHER PUBLICATIONS

Chemical Abstracts, vol. 116, No. 25, (Jun. 22, 1992), p. 792, col. 2, No. 255614j.

Jacquier et al, Bulletin de la Societe Chimique de France, No. 3, 1971, pp. 1040–1050.

*Primary Examiner*—Jacqueline Haley
*Attorney, Agent, or Firm*—Fisher, Christen & Sabol

[57] ABSTRACT

A process for the production of 2-substituted 5-chlorimidazole-4-carbaldehydes of the general formula:

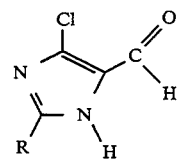

wherein R is hydrogen, an alkyl group, and alkenyl group, a cycloalkyl group, a benzyl group, a phenyl group or an aryl group. These compounds form important intermediate products for the production of antihypertensive pharmaceutical agents or herbicidal compounds.

16 Claims, No Drawings

PROCESS FOR THE PRODUCTION OF 2-SUBSTITUTED 5-CHLORIMIDAZOLE-4-CARBALDEHYDES

This is a continuation-in-part of U.S. Ser. No. 08/203,583, filed on Mar. 1, 1994 now abandoned.

BACKGROUND OF THE INVENTION

1. Field Of The Invention

The invention relates to a process for the production of 2-substituted 5-chlorimidazole-4-carbaldehydes of the general formula:

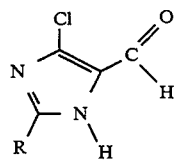   I wherein R is hydrogen, an alkyl group, an alkenyl group, a cycloalkyl group, a benzyl group, a phenyl group or an aryl group. The invention also relates to certain 2-substituted 3,5-dihydroimidazolin-4-ones.

2. Background Art

Several methods for the production of the above-mentioned compounds according to general formula I are known.

U.S. Pat. No. 4,355,040 describes a process according to which 2-amino-3,3-dichloro-acrylonitrile is reacted with an aldehyde to the corresponding azomethine intermediate product and further with a hydrogen halide and water to the 2-substituted 5-haloimidazole-4-carbaldehyde. Experimental data is lacking in the patent. A great drawback of the synthesis is that the 2-amino-3,3-dichloroacrylonitrile used first has to be produced starting from dichloroacetonitrile by its reaction with hydrogen cyanide/sodium cyanide. The extremely toxic reactants and the safety measures associated therewith that are already necessary for the preparation of the initial product, make the entire process unsuitable for industrial-scale production.

U.S. Pat. No. 4,355,040 discloses in another variant a 3-stage process, in which, in a first stage, an amidinehydrochloride is cyclized with high $NH_3$ pressure with dihydroxyacetone, the imidazole alcohol is halogenated and finally oxidized to the aldehyde.

It has turned out that pressures of over 20 bars are necessary for the cyclization reaction.

The oxidation of the alcohol works according to U.S. Pat. No. 4,355,040 in the presence of chromium oxide. It is obvious that an oxidation with heavy metal oxides, that are not recyclable as a rule, is no longer justifiable from present ecological aspects and requirements.

BROAD DESCRIPTION OF THE INVENTION

The main objective of the invention is to provide processes that do no have the above-mentioned drawbacks of the prior art. The main objective of the invention is achieved by the new process of the invention for the production of 2-substituted 5-chlorimidazoles, and the new 2-substituted 3,5-dihydroimidazol-4-ones of the invention.

Other objectives and advantages of the invention are set out herein or are obvious herefrom to one skilled in the art. The other objectives and advantages of the invention are achieved by the compounds and process of the invention.

The invention involves a process for the production of 2-substituted 5-chlorimidazole-4-carbaldehydes of the general formula:

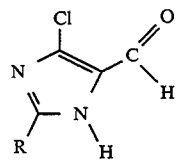   I wherein R is hydrogen, an alkyl group, an alkenyl group, a cycloalkyl group, a benzyl group, a phenyl group or an aryl group. The process includes, in the first stage, reacting a glycine ester hydrohalide of the general formula:

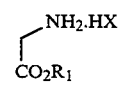   II wherein $R_1$ is an alkyl group and X is a halogen atom, with an imidic acid ester of the general formula:

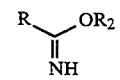   III wherein R has the above-mentioned meaning and $R_2$ is an alkyl group, in the presence of a base to provide the 2-substituted 3,5-dihydroimidazole-4-one of the general formula:

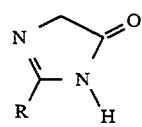   IV wherein R has the above-mentioned meaning and, in the second stage, is further reacted with phosphoroxy chloride in the presence of N,N-dimethylformamide to the end product.

Preferably an alkali hydroxide or an alkali alcoholate is used as the base in the first stage. Preferably the reaction in the first stage is performed in a pH range between 7 and 12. Preferably the reactants of the first stage, namely, the glycine hydrohalide, the imidic acid ester and the base, are reacted in the stochiometric molar ratio of 1:1:1. Preferably the reaction temperature in the first stage is between −20° and 50° C. Preferably the reactants of the second stage, namely, the 2-substituted 3,5-dihydroimidazol-4-one, the phosphoroxy chloride and the N,N-dimethylformamide, are reacted in a molar ratio of 1:1:1 to 1:5:5. Preferably the reaction temperature in the second stage is betwen 50° and 130° C.

Preferably the 2-substituted 3,5-dihydroimidazol-4-one of the general formula IV is not isolated in the course of the process.

The invention also involves 2-substituted 3,5-dihydroimidazol-4-ones of the general formula IV wherein R is n-propyl, n-butyl, 2-butenyl or 3-butenyl.

The 2-substituted 5-chlorimidazole-4-carbaldehydes of the general formula I are important initial products for the production of antihypertensive pharmaceutical agents (U.S. Pat. No. 4,355,040) or herbicial compounds (German OS 2804435).

DETAILED DESCRIPTION OF THE INVENTION

For the production of the 2-substituted 5-chlorimidazole-4-carbaldehydes of the general formula I, in the first stage, a glycine ester hydrohalide of the general formula:

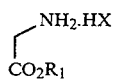

wherein $R_1$ is an alkyl group and X is a halogen atom, is reacted with an imidic acid ester of the general formula:

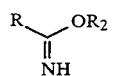

wherein R has the abaove-mentioned meaning and $R_2$ is an alkyl group, is reacted in the presence of a base to the 2-substituted 3,5-dihydroimidazol-4-one of the general formula:

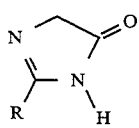

wherein R has the above-mentioned meaning.

The general designations of the groups in the substituents R, $R_1$ and $R_2$ have the following meanings.

An alkyl group is a straight-chain or branched $C_1$–$C_6$-alkyl group which is understood to be, for example, methyl, ethyl, propyl, isopropyl, n-butyl, sec.-butyl, tert.-butyl, pentyl or hexyl groups. The n-propyl group or the n-butyl group is the preferred alkyl group for R.

An alkenyl group is a straight-chain or branched $C_1$–$C_6$-alkenyl group which is understood to be, for example, 1-propenyl, 2-propenyl, 1-butenyl, 2-butenyl, 3-butenyl, pentenyl and its isomers or hexenyl and its isomers. The 2 or 3-butenyl group is the preferred alkenyl group for R.

Representatives of cycloalkyl groups are cyclopropyl, cyclobutyl, cyclopentyl or cyclohexyl groups.

Both the benzyl group and the phenyl group can contain substituents, such as, the above-mentioned alkyl groups, halogen atoms, nitro groups or amino groups.

Suitably chlorine, bromine or iodine, preferably chlorine, is understood by the designation halogen.

Suitably the procedure is that the glycine ester hydrohalide of the general formula II is reacted in the presence of a base suitably at a pH of 7 to 12, preferably 9 to 11, with the imidic acid ester of the general formula III. The glycine ester hydrohalides of the general formula II are commercially obtainable stable compounds. Suitable bases are the alkali hydroxides, such as, sodium hydroxide or potassium hydroxide, or alkali alcoholates such as, sodium or potassium methylate, ethylate or tert.butylate. Advantageously the base is available dissolved in a suitable solvent. Especially suitable are aliphatic alcohols, such as, methanol or ethanol. The imidic acid ester is suitably also added in the form of a solution in an inert solvent. Generally aromatic solvents are especially well suited for this purpose (i.e., the inert solvent), such as, toluene or chlorobenzene or the above-mentioned aliphatic alcohols.

Advantageously the reaction of the reactants glycine hydrohalide, imidic acid ester and base takes place in the stochiometric ratio of 1:1:1. The reaction temperature suitably ranges in the area of −20° to 50° C., preferably at 0° to 25° C.

After a reaction time of a few hours, the corresponding 2-substituted 3,5-dihydroimidazol-4-one of the general formula IV can be isolated by one skilled in the art, generally by simple filtration, in yields greater than 95 percent.

Advantageously the resultant reaction mixture is prepared without isolation of the 2-substituted 3,5-dihydroimidazol-4-one for further processing to the corresponding 5-chlorimidazole-4-carbaldehyde (one-pot process).

The compounds of the general formula IV resultant in the context of this stage, wherein R is n-propyl, n-butyl, 2-butenyl or 3-butenyl, are especially preferred. These compounds are not known in the literature and are, therefore, also a component of the invention.

This first stage of the process according to the invention contains a tremendous improvement of the known process according to R. Jacquier et al., Bull. Soc. Chim. France, (1971), 1040, which comprises the reaction of a free glycine ester with an imidic acid ethyl ester of the general formula III (R is illustrated only for methyl, phenyl, benzyl) in the absence of a solvent to the corresponding 3,5-dihydroimidazol-4-one. Disadvantageous in this known process is the fact that the free glycine ester is very unstable and, therefore, in each case must be newly synthesized and isolated for every reaction. According to the known process, after a reaction time of 24 hours and more, yields of only 30 to 48 percent could be obtained.

In the second stage, the reaction to the desired 2-substituted 5-chlorimidazole-4-carbaldehyde of general formula I takes place according to the invention with phosphoroxy chloride or phosgene in the presence of N,N-dimethylformamide. Suitably the molar ratio of the reactants 2-substituted 3,5-dihydroimidazol-4-one to phosphoroxy chloride or phosgene to N,N-dimethylformamide is in the range between 1:1:1 and 1:5:5, preferably at approximately 1:3:3. The reaction temperature is suitably between 50° and 130° C. Optionally, the second stage reaction can be conducted in the presence of an additional inert solvent.

The isolation of the resultant 2-substituted 5-chlorimidazole-4-carbaldehyde from the reaction mixture takes place advantageously in ways known to one skilled in the art by its extraction with a suitable solvent.

EXAMPLE 1

Production of 2-n-butyl-3,5-dihydroimidazole-4-one 31.71 g (0.25 mol) of glycine methyl ester hydrochloride was added to a solution of 10.1 g (0.25 mol) of sodium hydroxide in methanol at 0° C. After 15 minutes, 126.5 g of a 22.8 percent solution of pentanimidic acid methyl ester in chlorobenzene was instilled for 5 minutes in the white suspension. The light yellow suspension was stirred for 4 hours at room temperature and diluted with chlorobenzene (100 ml). The methanol was distilled off at a temperature of 26° C. and a pressure of 30 to 50 mbar, and the orange suspension was diluted with methylene chloride (100 ml) and then filtered. After removal of the solvent from the filtrate, 34.09 g (97 percent) of the title compound (content >95 percent, according to GC and $^1$H-NMR) was obtained. Data regarding the product was:

| $^1$H-NMR (CDCl$_3$, 300 Mhz) δ in ppm | 0.95 (t, 3H); |
|---|---|
| | 1.45 (m, 2H); |
| | 1.68 (m, 2H); |
| | 2.48 (t, 2H); |
| | 4.1 (m, 2H); |
| | 9.3 (br. s, 1H). |

EXAMPLE 2

Production of
2-n-butyl-5-chlorimidazole-4-carbaldehyde 2-n-Butyl-2-imidazolin-5-one (9.81 g, 70 mmol) was added to a solution of phosphoroxychloride (26.83 g, 175 mmol) in chlorobenzene (50 ml) at room temperature. The orange suspension was heated to 100° C. within 5 minutes, and then N,N-dimethylformamide (12.79 g, 175 mmol) was added within 3 minutes. The black mixture was kept for 2 hours at 100° C., cooled to 40° C. and poured on water (84 ml). After addition of ethyl acetate (42 ml), the mixture was stirred for 15 minutes at 26° to 28° C. and then adjusted to pH 7 by addition of 30 percent sodium hydroxide solution (67 ml). The phases were separated, and the aqueous phase was extracted twice with 70 ml of ethyl acetate each. The combined organic phases were dried (MgSO$_4$), filtered and concentrated by evaporation on a Rotavapor. The title compound was obtained in a yield of 8.31 g (64 percent) relative to the 2-n-butyl-2-imidazolin-5-one.

EXAMPLE 3

Production of
2-n-butyl-5-chlorimidazole-4-carbaldehyde (Process without isolation of 2-n-butyl-2-imidazolin-5-one)

31.71 g (0.25 mol) of glycine methyl ester hydrochloride as solid was added in one portion to a solution, which had been cooled to 0° C., of 10.17 g (0.25 mol) of sodium hydroxide in methanol (80 ml), and the white suspension (NaCl precipitates out) cooled to −8° C. The temperature rose to 0° C. within 15 minutes, then 127.0 g of a 22.68 percent solution of pentanimidic acid methyl ester in chlorobenzene (0.25 mol of pentanimidic acid methyl ester) was added for 15 minutes. The temperature was allowed to rise within 1 hour to 21° C., and then the yellowish brown suspension was stirred for 3.5 hours at 21° C. After addition of chlorobenzene (400 ml), approximately 240 g of a mixture of methanol, water and chlorobenzene was distilled off at 30° C. Phosphoroxy chloride (107.33 g, 0.7 mol) was added to the remaining suspension (about 420 g) (temperature rose to 35° C.). The cloudy, orange reaction mixture was heated to 100° C., and then N,N-dimethylformamide (51.71 g, 0.70 mol) was instilled for 5 minutes (the temperature rose to 108° C.). After 2 hours at 100° C. the black mixture was cooled to 75° C. and poured into 300 g of water which had been cooled to 10° C. The mixture was diluted with ethyl acetate (150 ml), stirred for 15 minutes at 50° C. and then adjusted to pH 1 by the addition of 160 ml of 30 percent sodium hydroxide solution. The phases were separated, and the aqueous phase was extracted twice with 250 ml of ethyl acetate each. The combined organic phases were dried (MgSO$_4$), filtered and concentrated by evaporation on a Rotavapor. The title compound was obtained in a yield of 34.3 g (73 percent), relative to the glycine methyl ester hydrochloride.

EXAMPLE 4

Production of
2-n-butyl-5-chlorimidazole-4-carbaldehyde (Process without isolation of 2-n-butyl-2-imidazolin-5-one)

31.72 g (0.25 mol) of glycine methyl ester hydrochloride as a solid was added in one portion to a solution, which had been cooled to 0° C., of 10.15 g (0.25 mol) of sodium hydroxide in methanol (80 ml) and the white suspension (NaCl precipitated out) cooled to −9° C. The temperature rose to 0° C. within 15 minutes, and then 127.0 g of a 22.68 percent solution of pentanimidic acid methyl ester in chlorobenzene (0.25 mol of pentanimidic acid methyl ester) was added for 15 minutes. The temperature was allowed to rise within 1 hour to 21° C., and then the yellowish brown suspension was stirred for 3.5 hours at 21° C. After addition of chlorobenzene (200 ml), approximately 210 g of a mixture of methanol, water and chlorobenzene was distilled off at 30° C. Phosphoroxy chloride (107.33 g, 0.70 mol) was added to the remaining suspension (about 226 g) (temperature rose to 35° C.). The cloudy, orange reaction mixture was heated to 100° C., and then DMF (51.71 g, 0.70 mol) was instilled for 5 minutes (the temperature rose to 108° C.). After 2 hours at 100° C., the black mixture was cooled to 40° C. and poured in 300 g of water which had been cooled to 10° C. The mixture was diluted with ethyl acetate (150 ml), heated for 15 minutes at 50° C. and adjusted to pH 1 by addition of 160 ml of 30 percent sodium hydroxide solution. The phases were separated, and the aqueous phase was extracted twice with 250 ml of ethyl acetate each. The combined organic phases were dried (MgSO$_4$), filtered and concentrated by evaporation on a Rotavapor to 125 g and cooled to −10° C. The precipitated product was filtered off, washed with cold ethyl acetate and dried at 50° C. The yield was 19.01 g (40 percent relative to the glycine methyl ester hydrochloride). The mother liquor contained, according to GC with internal standard, another 11.66 g of the title compound, thus the total yield was 65 percent relative to the glycine methyl ester hydrochloride.

EXAMPLE 5

Production of 2-n-propyl-3,5-dihydroimidazol-4-one 17.39 g (138 mmol) of glycine methyl ester hydrochloride was added to a solution of sodium hydroxide (5.56 g, 139 mmol) in methanol (55 ml) at 0° C. After 15 minutes, 14.50 g (content 96.3 percent, 138 mmol) of butanimidic acid methyl ester was instilled in the white suspension for 8 minutes. The mixture was stirred for 3 hours at room temperature and then concentrated by evaporation on a Rotavapor. The residue was mixed with CH$_2$Cl$_2$ (250 ml) and the resultant suspension was filtered. The filtrate was concentrated by evaporation on a Rotavapor, again mixed with CH$_2$Cl$_2$ (250 ml) and filtered again. After removal of the solvent, the title compound was obtained (15.13 g, content >95 percent according to $^1$H-NMR, 83 percent yield). Other data concerning the product was:

| $^1$H-NMR (CDCl$_3$, 400 Mhz) δ in ppm | 1.03 (t, 3H); |
|---|---|
| | 1.75 (m, 2H); |
| | 2.46 (t, 2H); |
| | 4.12 (s, 2H); |
| | 9.98 (br. s, 1H). |

EXAMPLE 6

Production of 2-n-propyl-5-chlorimidazole-4-carbaldehyde

N,N-dimethylformamide (7.04 g, 96.3 mmol) was added to a mixture of 2-n-propyl-3,5-dihydroimidazol-4-one (4.49 g, 35.6 mmol) and POCl$_3$ (14.76 g, 96.3 mmol) in chlorobenzene (40 ml) at 100° C. The mixture was heated for 2 hours at 100° C., cooled and poured on 40 g of ice. The mixture was adjusted to pH 1 by the addition of 30 percent sodium hydroxide solution (22.5 ml) and the phases were separated. The aqueous phase was extracted twice with 40 ml of ethyl acetate each and the combined organic phases were washed with water (20 ml) and filtered on silica gel. After removal of the solvent from the filtrate, 2.79 g of a light brown solid was obtained. Recrystallization from ethyl acetate/petroleum ether yielded the title compound (2.04 g, 33 percent). The product had a melting point of 133.3° to 137.5° C. Other data concerning the product was:

| $^1$H-NMR (CDCl$_3$, 400 Mhz) δ in ppm | 1.01 (t, 3H); |
|---|---|
| | 1.84 (m, 2H); |
| | 2.83 (t, 2H); |
| | 9.64 (s, 1H); |
| | 11.56 (br. s, 1H). |

EXAMPLE 7

Production of 2-but-2-enyl-3,5-dihydroimidazol-4-one

Corresponding to Example 1, the title product was produced by reaction of glycine methyl ester hydrochloride and 3-pentenimidic acid methyl ester. Data concerning the product was:

| $^1$H-NMR (CDCl$_3$, 400 Mhz) δ in ppm | 1.75 (d, 3H); |
|---|---|
| | 3.19 (d, 2H); |
| | 4.12 (s, 2H); |
| | 5.54 (m, 1H); |
| | 5.75 (m, 1H); |
| | 9.20 (br. s, 1H). |

What is claimed is:

1. A process for the production of a 2-substituted 5-chlorimidazole-4-carbaldehyde of the general formula:

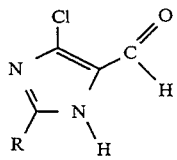

wherein R is hydrogen, an alkyl group, an alkenyl group, a cycloalkyl group, a benzyl group or a phenyl group, comprising, in a first stage, reacting a glycine ester hydrohalide of formula:

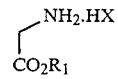

wherein R$_1$ is an alkyl group and X is a halogen atom, with an imidic acid of formula:

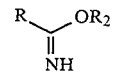

wherein R has the above-mentioned meaning and R$_2$ is an alkyl group, in the presence of a base and a solvent to produce a 2-substituted 3,5-dihydroimidazol-4-one of formula:

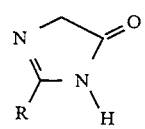

wherein R has the above-mentioned meaning, and in a second stage, the 2-substituted 3,5-dihydroimidazol-4-one of formula IV is reacted with phosphoroxy chloride or phosgene and N,N-dimethylformamide to provide the end product.

2. The process according to claim 1 wherein an alkali hydroxide or an alkali alcoholate is used as the base in the first stage.

3. The process according to claim 2 wherein the reactants of the first stage, glycine hydrohalide, imidic acid ester and base are reacted in a stochiometric molar ratio of about 1:1:1.

4. The process according to claim 3 wherein the reactants of the first stage glycine hydrohalide, imidic acid ester and base are reacted in a stochiometric molar ratio of about 1:1:1.

5. The process according to claim 4 wherein the reaction in the first stage is conducted at a temperature between −20° and 50° C.

6. The process according to claim 5 wherein the reactants of the second stage, 2-substituted 3,5-dihydroimidazol-4-one, phosphoroxy chloride or phosgene, and N,N-dimethylformamide are reacted in a molar ratio of 1:1:1 to 1:5:5.

7. The process according to claim 6 wherein the reaction in the second stage is conducted at a temperature of between 50° and 130° C.

8. The process according to claim 1 wherein the reaction in the first stage is performed in a pH range between 7 and 12.

9. The process according to claim 1 wherein the reactants of the first stage, glycine hydrohalide, imidic acid ester and base are reacted in a stochiometric molar ratio of about 1:1:1.

10. The process according to claim 1 wherein the reaction in the first stage is conducted at a temperature between −20° and 50° C.

11. The process according to claim 1 wherein the reactants of the second stage 2-substituted 3,5-dihydroimidazol-4-one, phosphoroxy chloride or phosgene, and N,N-dimethylformamide are reacted in a molar ratio of 1:1:1 to 1:5:5.

12. The process according to claim 1 wherein the reaction in the second stage is conducted at a temperature between 50° and 130° C.

13. The process according to claim 1 wherein the 2-substituted 3,5-dihydroimidazol-4-one of the general formula IV is not isolated in the course of the process.

14. The process according to claim 1 wherein, in the first stage, the solvent is an aliphatic alcohol, toluene or chlorobenzene.

15. The process according to claim 1 wherein, in the first stage, the imidic acid ester of formula III is added to the glycine ester hydrohalide of formula II, the base and the solvent.

16. A 2-substituted 3,5-dihydroimidazol-4-one of formula:

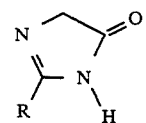

wherein R is 2-butenyl or 3-butenyl.

* * * * *